(12) United States Patent
Jensen et al.

(10) Patent No.: US 11,739,549 B2
(45) Date of Patent: *Aug. 29, 2023

(54) SMART POOL SKIMMER WITH CLOUD-BASED POOL MONITORING SYSTEM

(71) Applicant: KETO A.I, INC., Houston, TX (US)

(72) Inventors: Jeffrey S. Jensen, Houston, TX (US); Andrew D. Higgins, Houston, TX (US)

(73) Assignee: KETO A.I, INC., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/661,117

(22) Filed: Apr. 28, 2022

(65) Prior Publication Data
US 2022/0251862 A1    Aug. 11, 2022

Related U.S. Application Data

(63) Continuation of application No. 16/181,279, filed on Nov. 5, 2018, now Pat. No. 11,319,722.
(Continued)

(51) Int. Cl.
*E04H 4/12* (2006.01)
*G01N 33/18* (2006.01)
(Continued)

(52) U.S. Cl.
CPC .......... *E04H 4/1272* (2013.01); *E04H 4/1263* (2013.01); *G01C 9/00* (2013.01);
(Continued)

(58) Field of Classification Search
CPC ....... E04H 4/1272; E04H 4/1263; E04H 4/14; G01C 9/00; G01F 23/00; G01K 1/14; G01N 33/1886
See application file for complete search history.

(56) References Cited

U.S. PATENT DOCUMENTS 4,630,634 A    12/1986   Sasaki et al.
5,369,623 A    11/1994   Zerangue
(Continued)

FOREIGN PATENT DOCUMENTS

| CN | 2054047383 | 7/2016 |
|---|---|---|
| WO | 2016/110753 A1 | 7/2016 |
| WO | 2016176169 A1 | 11/2016 |

OTHER PUBLICATIONS

Waterguru: How it Works, <https://waterguru.com/how-it-works.html>, retrieved Mar. 12, 2019.
(Continued)

*Primary Examiner* — Bradley R Spies
*Assistant Examiner* — Jeannie McDermott
(74) *Attorney, Agent, or Firm* — Patterson + Sheridan, LLP

(57) ABSTRACT

A smart pool skimmer is disclosed. In one embodiment, the pool skimmer includes a body housing having electronics and sensors extending from the body housing to monitor pool conditions. The sensors detect a plurality of pool condition, including but not limited to pH, ORP, temperature, water level, water movement, chlorine levels, and salt concentration. The smart pool skimmer receives data from the sensors and sends the information to a user computing device or a cloud-based analytics server, which tracks conditions of the pool water. A solar panel may be provided on the housing to enable the smart skimmer to run on renewable energy. Additionally, visual light indicators can be mounted on top of the cover plate to provide visual indications of pool conditions.

20 Claims, 7 Drawing Sheets

Related U.S. Application Data

(60) Provisional application No. 62/582,104, filed on Nov. 6, 2017.

(51) Int. Cl.
*G01C 9/00* (2006.01)
*G01F 23/00* (2022.01)
*G01K 1/14* (2021.01)

(52) U.S. Cl.
CPC ............... *G01F 23/00* (2013.01); *G01K 1/14* (2013.01); *G01N 33/1886* (2013.01)

(56) References Cited

U.S. PATENT DOCUMENTS

| | | |
|---|---|---|
| 5,551,191 A | 9/1996 | Maiwandi |
| 8,459,100 B2 | 6/2013 | Biberger |
| 9,034,193 B2 | 5/2015 | Shalon |
| 9,776,888 B1 | 10/2017 | Kurani et al. |
| 9,834,451 B2 | 12/2017 | Miller et al. |
| 10,150,680 B1 | 12/2018 | Kurani et al. |
| 2009/0120856 A1 | 5/2009 | Meagher |
| 2009/0139019 A1 | 6/2009 | Shebek et al. |
| 2010/0188236 A1 | 7/2010 | Biberger |
| 2011/0056940 A1 | 3/2011 | Goffman |
| 2017/0026547 A1 | 1/2017 | Esumi |
| 2017/0092096 A1 | 3/2017 | Fernandes et al. |
| 2017/0098361 A1 | 4/2017 | Sentosa et al. |
| 2017/0209339 A1 | 7/2017 | Potucek et al. |

OTHER PUBLICATIONS

Phin: Homepage, <https://www.phin.co/>, retrieved Mar. 12, 2019.
International Search Report—PCT/US2018/059287—International Searching Authority—Korean Patent Office—dated May 24, 2019, 3 pages.

SMART POOL SKIMMER WITH CLOUD-BASED POOL MONITORING SYSTEM

CROSS-REFERENCE TO RELATED APPLICATIONS

This application is a continuation of U.S. application Ser. No. 16/181,279, entitled "Smart Pool Skimmer with Cloud Based Pool Monitoring System" which claims the benefit of U.S. Provisional Application No. 62/582,104, entitled "Smart Pool Skimmer with Cloud Based Pool Monitoring System" filed on Nov. 6, 2017, and assigned to the assignee hereof, the content of which is hereby incorporated by reference in its entirety.

INTRODUCTION

Field of Disclosure

Aspects of the present disclosure relate to monitoring pool conditions, and more particularly, to a smart pool skimmer that monitors pool conditions using a plurality of sensors.

Description of Related Art

Improperly treated pool water leads to the proliferation of algae and bacteria in addition to other free radicals. Common water sanitation methods are based on chemical sanitizers which must be maintained at constant concentration levels for proper effectiveness.

At current, the most practical way to determine chemical balance of the pool water has been through chemical testing kits, or test strips by visual color indicators. This method requires that the actor manually take a water sample from the pool, apply an agent and reactant, and physically observe the color outcome compared to a reference color to determine the active chemical composition. Some electrical monitoring systems have begun to appear in the market, however; they feature floating apparatuses and that are capable of measuring pH and oxidation reduction potential (ORP).

Electronic sensors such as an ORP sensor have been successfully utilized as a standard for measuring water quality. Research has shown that an ORP value of 650 to 700 mV, free-floating decay and spoilage bacteria as well as pathogenic bacteria such as E. coli or Salmonella species are killed within 30 seconds. This skimmer plate, for example, takes advantage of the ORP process to determine chemical availability in the liquid or pool.

Pool water evaporation is a longstanding problem for pool owners. Studies have shown that pool water evaporation can exceed ¼ to ½ inch per day. Current products to maintain pool water level have proven unreliable and prone to failure over time, and add-on devices create an unsightly clutter of hoses and valves around the pool.

Solid state water level sensors are quickly becoming a standard for highly accurate water level measurements. The skimmer plate sits in a fixed and static position providing the skimmer plate an excellent opportunity to take highly accurate water level readings through in integrated design. Utilizing cloud-based machine learning, and an automated refill valve, predictive water level maintenance is achievable.

The primary function of a conventional pool skimmer cover plate is to prevent objects from falling into a pool filter basket. A pool skimmer cover plate typically provides a barrier to an otherwise open cylindrical hole near the pool. Partial purpose of this disclosure is to utilize the strategic location of the cover plate, and/or skimmer with a combination of electronic sensors and machine learning software to source and monitor data on pool water conditions compared to other aforementioned solutions that float in the water and are susceptible to problems, such as being caught in debris or the skimmer itself.

There are typically two suction points on common in-ground swimming pools, the floor suction and skimmer(s) suction. This solution is particularly applicable to the skimmer suction and/or covering plate of the pool skimmer.

BRIEF SUMMARY

The systems, methods, and devices of the disclosure each have several aspects, no single of which is solely responsible for its desirable attributes. Without limiting the scope of this disclosure as expressed by the claims which follow, some features will now be discussed briefly. After considering this discussion, and particularly after reading the section entitled "Detailed Description" one will understand how the features of this disclosure provide advantages that include a smart pool skimmer for monitoring pool conditions.

Certain aspects provide a smart pool skimmer in contact with pool water for monitoring conditions of the pool water. The smart pool skimmer includes a body housing with a top cover comprising a controller unit; at least one water-based sensor extending away from the body housing and connected to the controller unit, wherein the at least one sensor is in contact with the pool water; and a communication unit in communication with the controller unit. Other aspects provide that the smart pool skimmer may include an indicator light. The smart pool skimmer can detect pH, ORP, temperature, water level, water movement, chlorine levels, salt concentration, and other pool conditions. The smart pool skimmer can utilize Bluetooth, Wi-Fi or cellular service for communication, and can use a rechargeable battery, solar power, or any combination thereof. In one aspect, the body housing includes a sensor enclosure fairing for the at least one sensor. In another aspect, the smart pool skimmer further comprises an acoustic transducer.

Certain aspects provide for a system for monitoring pool conditions. The system generally includes a smart pool skimmer with one or more sensors, a cloud-based analytics server in communication with the pool skimmer using a computer network, wherein the cloud-based analytics server tracks conditions of the pool water; and a user device with a graphical user interface for visualization of trend-based conditions of the pool water.

Certain aspects provide for a method for monitoring pool conditions performed by an analytics server. The method generally includes receiving and storing information of a plurality of states of pool conditions from a smart pool skimmer, wherein the information comprises measurements from the smart pool skimmer; tracking changes between the plurality of states of pool conditions; and analyzing the changes between the plurality of states of pool conditions using machine learning algorithms to generate predictions regarding the pool conditions.

Certain aspects provide a method for monitoring pool conditions performed by a smart pool skimmer. The method generally includes detecting one or more of the pool conditions using one or more sensors of the smart pool skimmer; transmitting the one or more of the pool conditions to a cloud-based analytics server using a computer network; and receiving predictions regarding future pool conditions from the analytics server.

To the accomplishment of the foregoing and related ends, the one or more aspects comprise the features hereinafter fully described and particularly pointed out in the claims. The following description and appended drawings set forth in detail certain illustrative features of the one or more aspects. These features are indicative, however, of but a few of the various ways in which the principles of various aspects may be employed.

BRIEF DESCRIPTION OF THE DRAWINGS

So that the manner in which the above-recited features of the present disclosure can be understood in detail, a more particular description, briefly summarized above, may be had by reference to aspects, some of which are illustrated in the drawings. It is to be noted, however, that the appended drawings illustrate only certain typical aspects of this disclosure and are therefore not considered limiting of its scope, for the description may admit to other equally effective aspects.

To facilitate understanding, identical reference numerals have been used, where possible, to designate identical elements that are common to the figures. It is contemplated that elements disclosed in one aspect may be beneficially utilized on other aspects without specific recitation.

DETAILED DESCRIPTION

Aspects of the present disclosure provide apparatus and methods for a smart pool skimmer with cloud-based pool monitoring, which includes monitoring pool water, chemistry, water flow and level characteristics, wave interactions and obstructions in the skimmer and other environmental conditions of a pool or spa.

The following description provides examples, and is not limiting of the scope, applicability, or examples set forth in the claims. Changes may be made in the function and arrangement of elements discussed without departing from the scope of the disclosure. Various examples may omit, substitute, or add various procedures or components as appropriate. For instances, the methods described may be performed in an order different from that described, and various steps may be added, omitted, or combined. Also, features described with respect to some examples may be combined in some other examples. For example, an apparatus may be implemented or a method may be practiced using any number of the aspects set forth herein. In addition, the scope of the disclosure is intended to cover such an apparatus or method which is practiced using other structure, functionality, or structure and functionality in addition to, or other than, the various aspects of the disclosure set forth herein. It should be understood that any aspect of the disclosure disclosed herein can be embodied by one or more elements of a claim. The word "exemplary" is used herein to mean "serving as an example, instance, or illustration." Any aspect described herein as "exemplary" is not necessarily to be construed as preferred or advantageous over the other aspects.

The smart pool skimmer constructed in accordance with this disclosure includes a device designed as part of, or integrated with a pool skimmer. The smart pool skimmer may be sized and shaped to replace an existing skimmer cover plate for an in-ground or above ground pool. An exemplary embodiment of a smart pool skimmer designed to interface with an existing pool skimmer and a lower body enclosed with electronics and sensors to monitor conditions of the pool, is shown with reference to FIGS. 1A through 1D and FIG. 2. The arrangements as shown below illustrate an embodiment of the smart skimmer in the configuration of a skimmer cover plate.

Figure 1A:
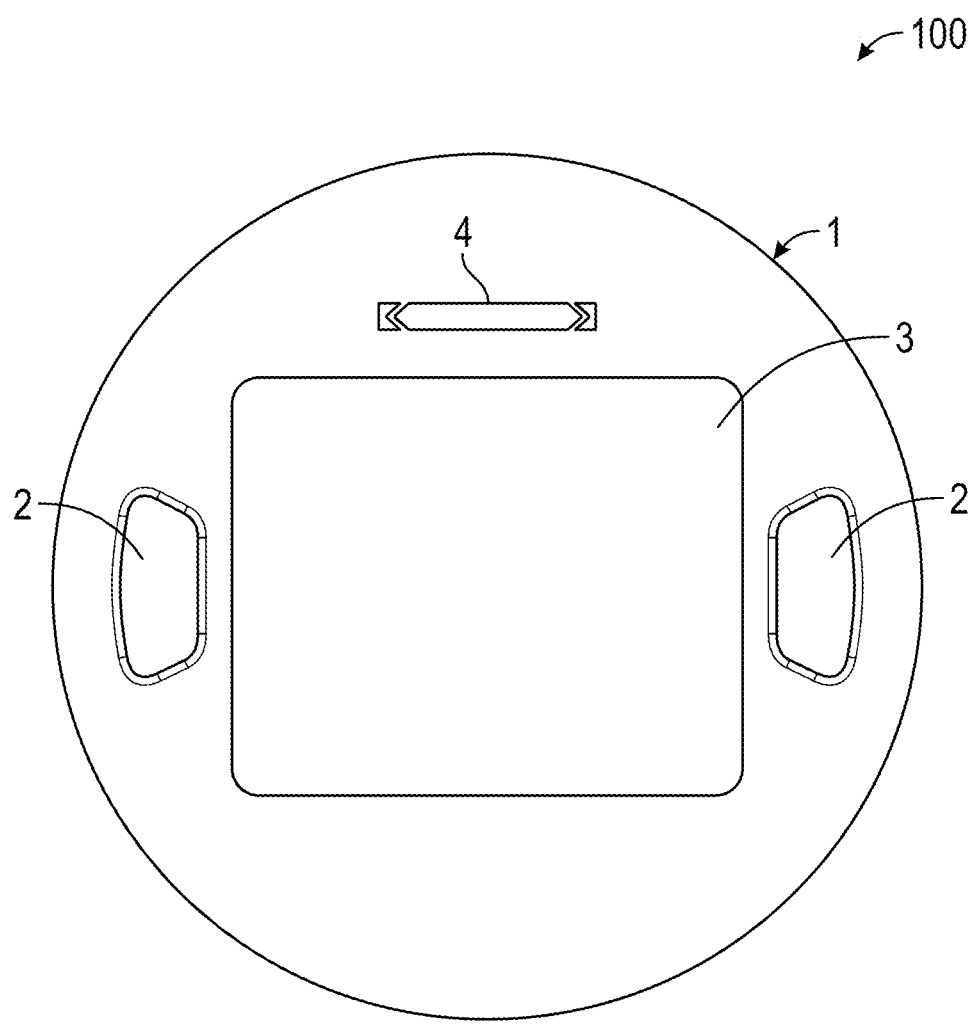
FIG. 1A is a top view of an exemplary embodiment of the smart pool skimmer, in accordance with certain aspects of the present disclosure.

FIG. 1A is a top view of an exemplary embodiment of the smart pool skimmer 100, in accordance with certain aspects of the present disclosure. In the exemplary embodiment, the smart pool skimmer 100 has a body housing that includes a body housing comprising a top cover 1, lifting slots 2, a solar panel 3 and indicator light pipe(s) 4. The solar panel 3 as shown is embedded into the top cover 1, sealed and connected to the underside electronics compartment, and in other embodiments, the solar panel 3 can be replaced by other mechanisms for charging a rechargeable battery or by replacing the power source of the smart pool skimmer 100. The lifting slots 2 provide a mechanism to lift the smart pool skimmer 100 from an existing skimmer.

Figure 1B:
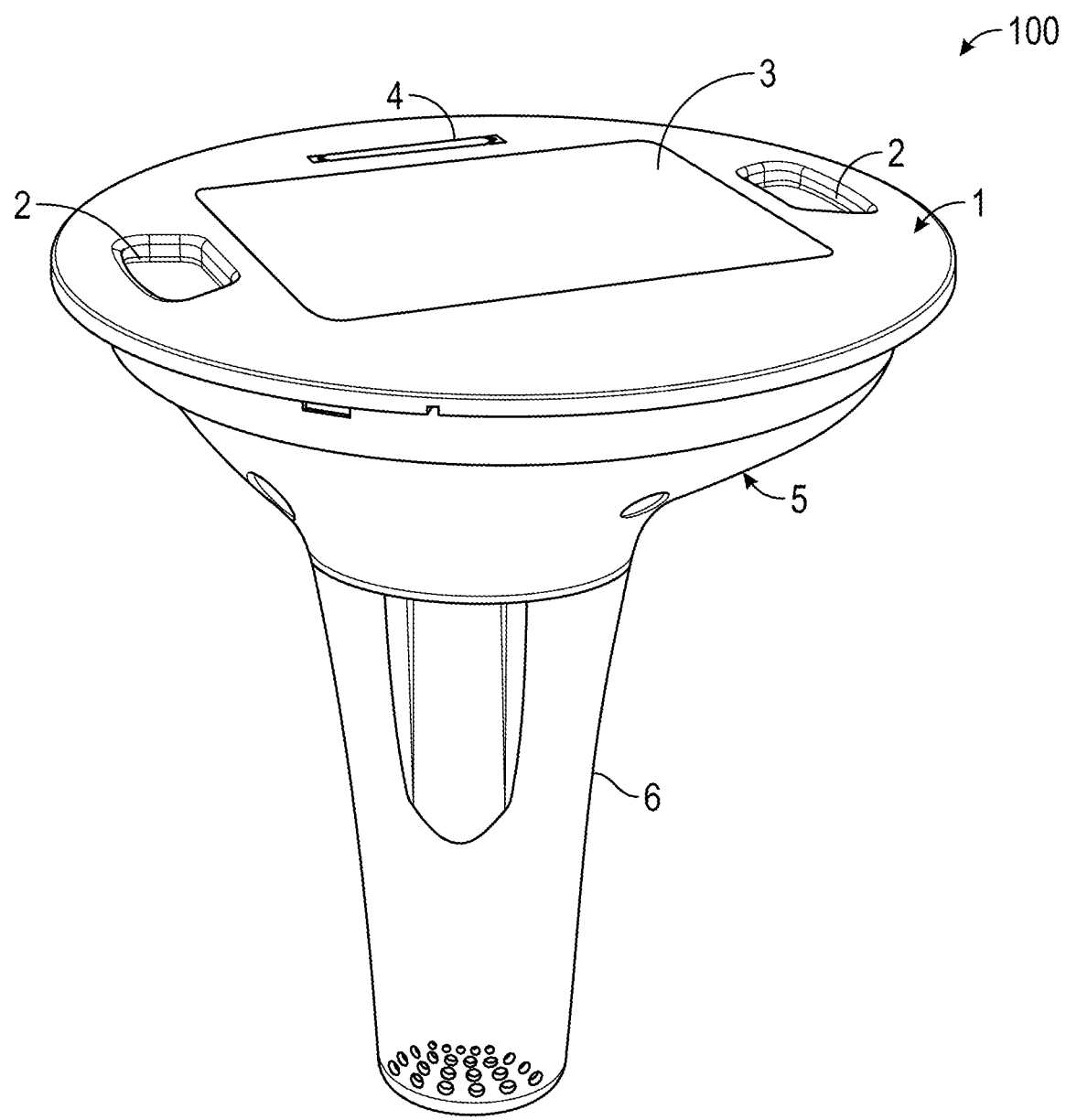
FIG. 1B is a top perspective view of an exemplary embodiment of the smart pool skimmer, in accordance with certain aspects of the present disclosure.

FIG. 1B is a top perspective view of an exemplary embodiment of the smart pool skimmer 100, in accordance with certain aspects of the present disclosure. FIG. 1B illustrates the sensor enclosure fairing (6) for sensors of the smart pool skimmer 100. This fairing comprises a non-watertight snap fit feature designed with vent holes to allow for the unobstructed flow of water. The fairing is also designed to prevent debris and unwanted materials from collecting around the sensors.

The sensors (not illustrated in FIG. 1B), which are both digital and analog depending on their function, provide information about pool conditions, including pool water chemistry, water flow, water lever characteristics, wave interactions, and obstructions in the skimmer and other environmental conditions of the pool or spa. All measurements are gathered from electronic signals which are generated from the sensor(s) that extend away from the body housing. A microcontroller (not illustrated in FIG. 1B) located inside the body housing connects to the sensors. The microcontroller stores data locally or sends the data to the cloud when a Wi-Fi, Bluetooth or cellular connection is present. The data is aggregated and stored in the cloud for further analysis and visualization of trend-based characteristics. Data aggregation, storage, and analysis in the cloud are discussed in further detail below.

In an exemplary embodiment, one of the sensors detects ORP. ORP is directly related to the concentration and activity of water sanitizer and has been recognized as a standard indicator of water quality and is used to inform the user about the state of water quality. The ORP readings in millivolts are translated into simple measurements for a homeowner or serviceman to determine whether the water is safe and whether chemicals need to be added or diluted. ORP sensors are currently available in market and can monitor water on a continuous basis with accuracy. They provide the oxidation-reduction potential of a sanitizer, such as chlorine or various other mechanisms. Since an ORP sensor measures the potential generated from the active form, versus the inactive form, they can provide a more accurate form of sanitation effectiveness.

The housing of the smart pool skimmer 100 is designed to accommodate one or more electronic sensors, which include, but are not limited to: ORP, pH, Temperature, Chlorine PPM, water level and wave interactions. In an exemplary embodiment, the electronic sensors provide feedback and information regarding pool characteristics wirelessly over the cloud through an antenna and digital radio system embedded in the microcontroller.

Additionally, the sensors can detect salt concentration, calcium, alkalinity, water current, light, motion, and sound. In one embodiment, sensors may extend from the body housing to receive and transmit acoustic signals, or water chemistry data. In some embodiments, the sensors can detect water level and wave characteristics that would indicate objects entering the pool, and the lower body is formed accordingly to allow for these sensors. These sensors include water level float switches and electronic solid state level sensors. In another embodiment, the sensors can include an accelerometer or tilt sensor to provide information about the state of the pool basket, such as the last time the pool basket was inspected or emptied.

In one exemplary embodiment, one of the sensors of the smart pool skimmer 100 is an acoustic sensor or an acoustic transmitter/receiver. In this embodiment, the acoustic sensor or transmitter/receiver can communicate with other submerged devices in the pool as an underwater data access point for access to the count. In one embodiment, the acoustic sensor or transmitter/receiver is strategically placed on the bottom or side of the pool or spa, and the acoustic sensor or transmitter/receiver transmits a signal to the smart pool skimmer 100 to indicate any acoustic changes in the pool or spa. Acoustic changes in the pool or spa can include people or objects entering or exiting the pool or spa.

In one exemplary embodiment, one of the sensors of the smart pool skimmer 100 is a solid-state water level sensor. The solid-state water level sensor determines the filter basket condition in the smart pool skimmer 100, and can also determine pool pump conditions. For example, as a skimmer basket fills with debris, water flow is restricted and gradually increases the level of water in the skimmer 100. The water level sensor can determine whether the filter basket is clogged or free of debris. Similarly, the water level sensor can detect whether the pool pump is on or off. In one embodiment, the smart pool skimmer 100 uses machine learning in order to accurately and precisely determine pool conditions based on the history of data from the sensors of the smart pool skimmer 100.

Figure 1C:
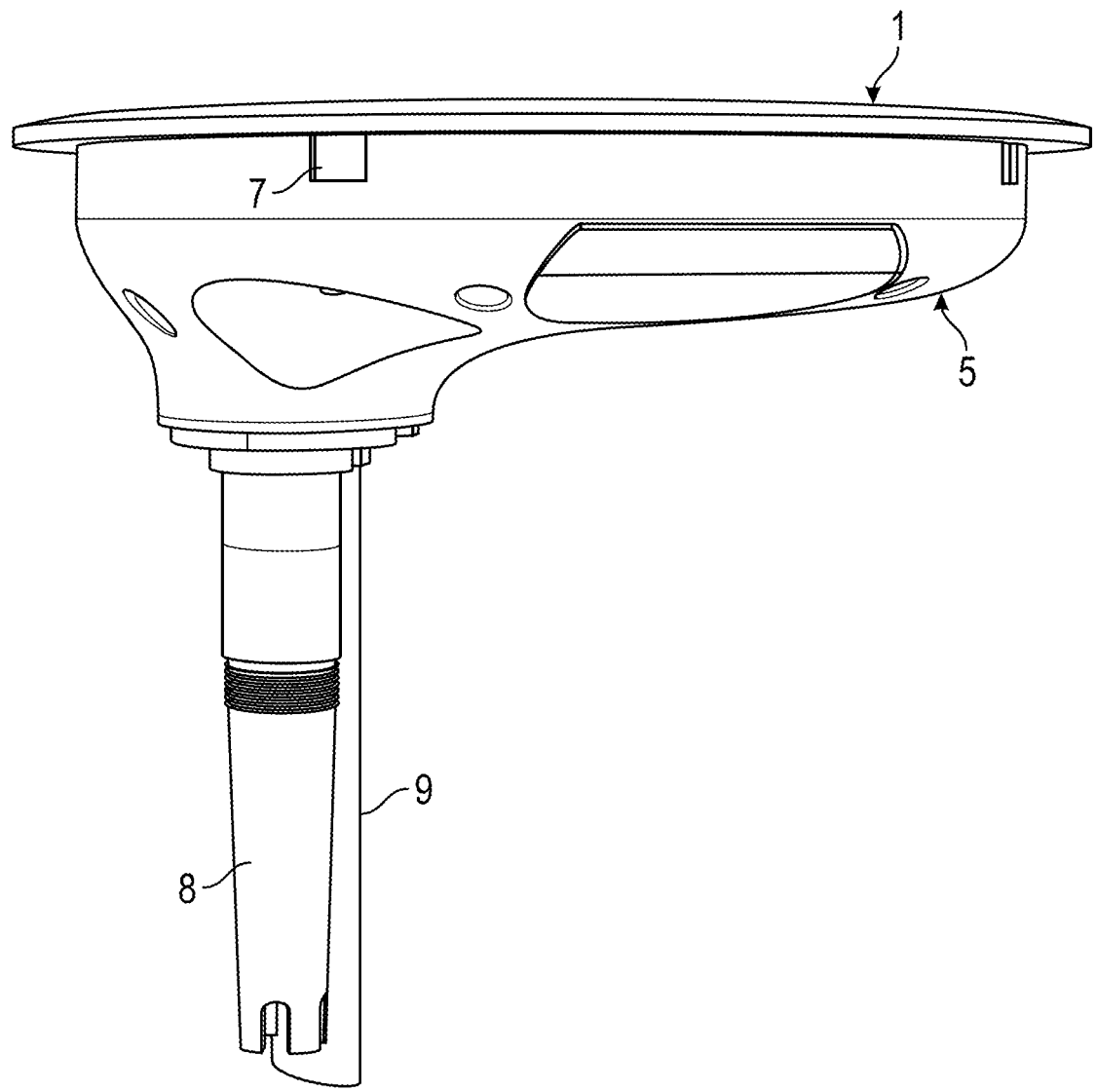
FIG. 1C is a side view of an exemplary embodiment of the smart pool skimmer, in accordance with certain aspects of the present disclosure.
Figure 1D:
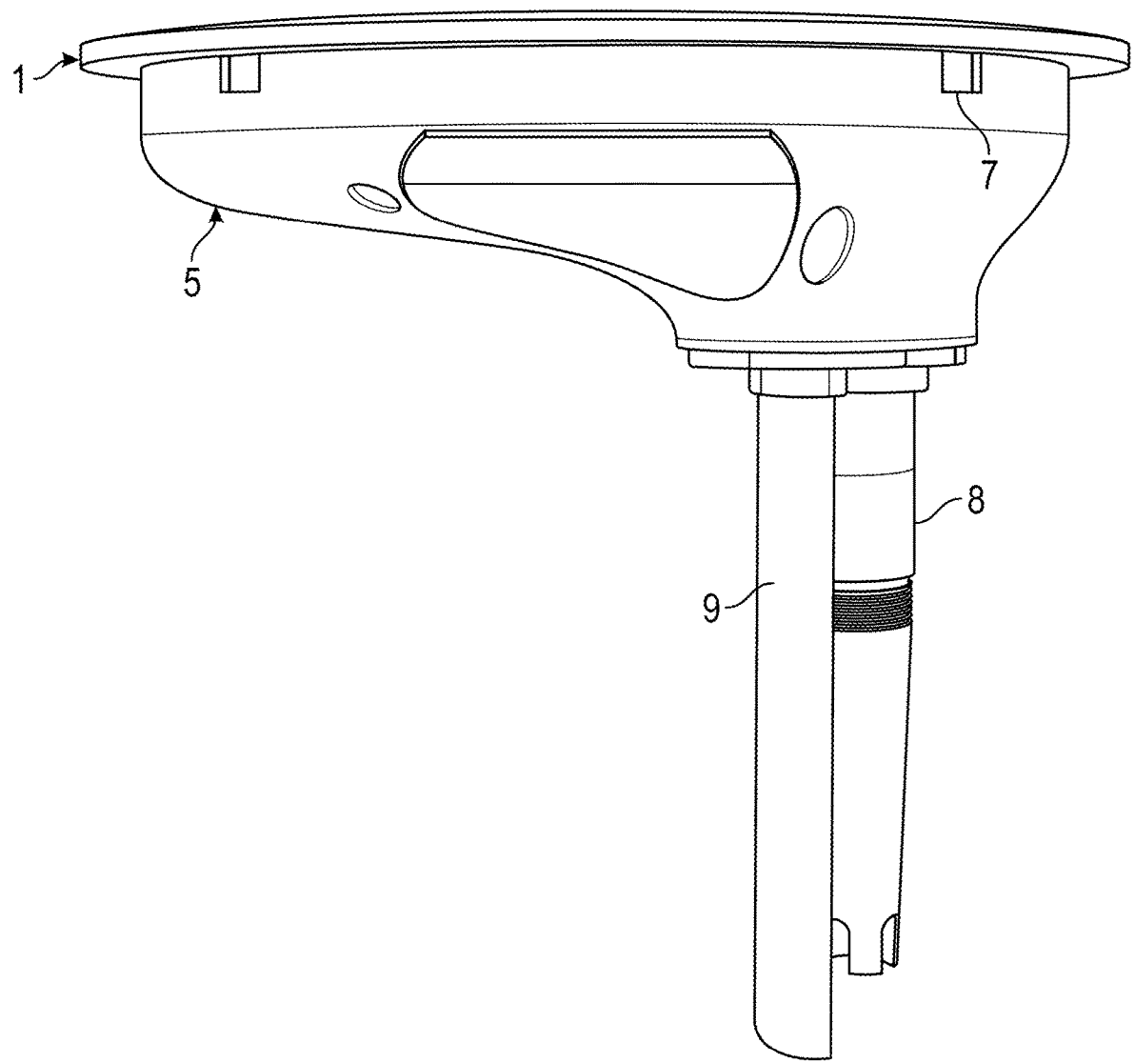
FIG. 1D is a side view of an exemplary embodiment of the smart pool skimmer, in accordance with certain aspects of the present disclosure.

FIGS. 1C and 1D are perspective views of the top cover and bottom cover (5) of an exemplary embodiment of the smart pool skimmer 100, in accordance with certain aspects of the present disclosure, with the sensor fairing removed for illustrative purposes. In the exemplary embodiment, the smart pool skimmer 100 uses an integrated ORP/pH/temperature sensor 8 and a water level/wave sensor 9. Each of the sensors are secured and sealed to the body housing. The body housing further comprises a bottom cover that is removable with thread forming screws and sealed when installed with a weathertight gasket. The exemplary embodiment of the smart pool skimmer 100 includes ultrasonic plastic weldments for a permanent seal between the top and bottom covers. The exemplary embodiment also includes securing clip recesses 7 that allow the smart pool skimmer 100 to be secured to universal adaptor collars.

In one embodiment, the smart pool skimmer 100 has one size which allows for configurable adaptor collars to accommodate various size pool skimmers. Each of these adaptor collars have universal inner dimensions that snap fit to the smart pool skimmer 100. The outer dimensions of the adaptor rings are sized to fit the overall majority of skimmers in the market.

The integrated ORP/pH/Temp sensor 8 can additionally be replaced and/or combined as a Chlorine (PPM) or salt indicator probe as required. As described above, additional sensors can be added to the smart skimmer 100 based on design variations, sensor consolidations and general improvements in sensor technology.

In an exemplary embodiment, the smart pool skimmer 100 monitors temperature using one of the sensors. A temperature probe is integrated with the ORP/pH/Temperature Sensor 8. Data analytics using the cloud-based machine learning software will process temperature and sunlight trends to determine, but not be limited to, unwanted scenarios, such as algae and other unwanted potential biological formations in the pool. Data analytics and cloud-based machine learning are discussed in detail below.

Due to the static position of the plate, pool water level can be monitored using a water level sensor 9. In this exemplary embodiment, the sensor will be in the form of a solid-state resistance sensor. This sensor may also have the ability to detect water interactions that reflect objects entering the water. This sensor therefore may have the capability to function as a pool alarm. Through the cloud-based software of a pool monitoring system, the smart pool skimmer informs the system user of objects that have entered the pool based on requirements or settings. The sensors can be enclosed in one or more plastic tubes for protection from dirt and debris. The protective tube can be adequately vented to prevent air pockets or other scenarios which could negatively affect measurements.

In one embodiment, the smart pool skimmer 100 functions as a pool water level and/or alarm device only. This reduces the capital investment of customers by reducing electronic equipment and complexity. Various design modifications may add and remove hardware, software and sensors to satisfy customer needs.

In one embodiment, the top cover 1 and bottom cover 5 are designed with a weathertight seal. In another embodiment, a watertight seal would be provided.

In the exemplary embodiment, the top cover 1 is designed with a recessed channel for a rubberized over-mold with a chemical or mechanical bond to create a gasket 14. The bottom cover is designed with a tapered edge 15 that compresses the gasket 14 for a weathertight seal. The bottom cover 5 and top cover 1 are secured with threaded stainless steel screws.

Figure 5:
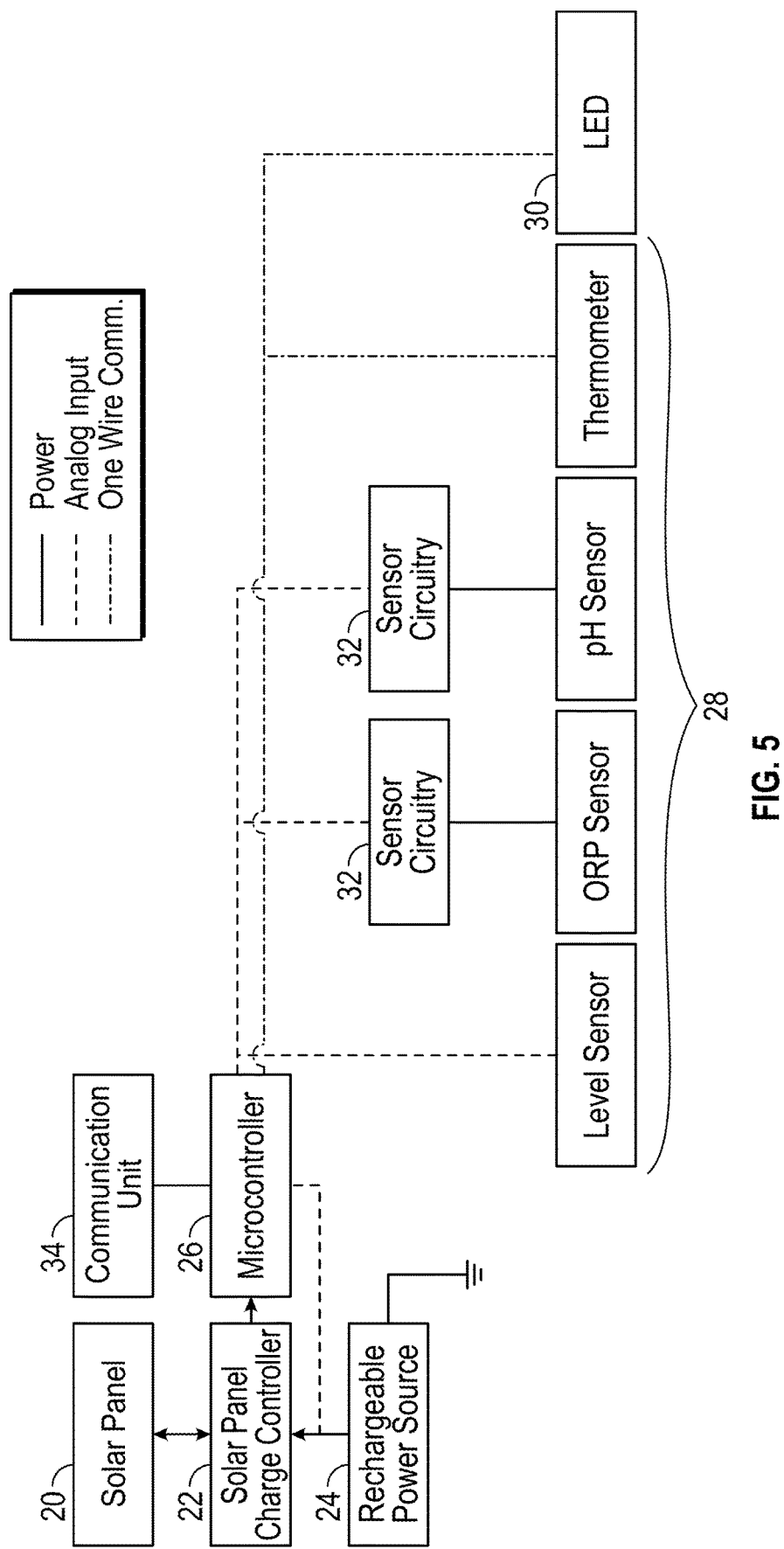
FIG. 5 illustrates an electronics architecture schematic of an exemplary embodiment of the smart pool skimmer, in accordance with certain aspects of the present disclosure.

In the exemplary embodiment, the bottom cover 5 is equipped with a micro or mini USB charging and communication port for connection to the communication unit discussed in reference to FIG. 5. The function of this port is for initial setup, charging, troubleshooting and downloading of locally stored data. Another embodiment of this design includes a waterproof reset tactile switch.

Figure 2:
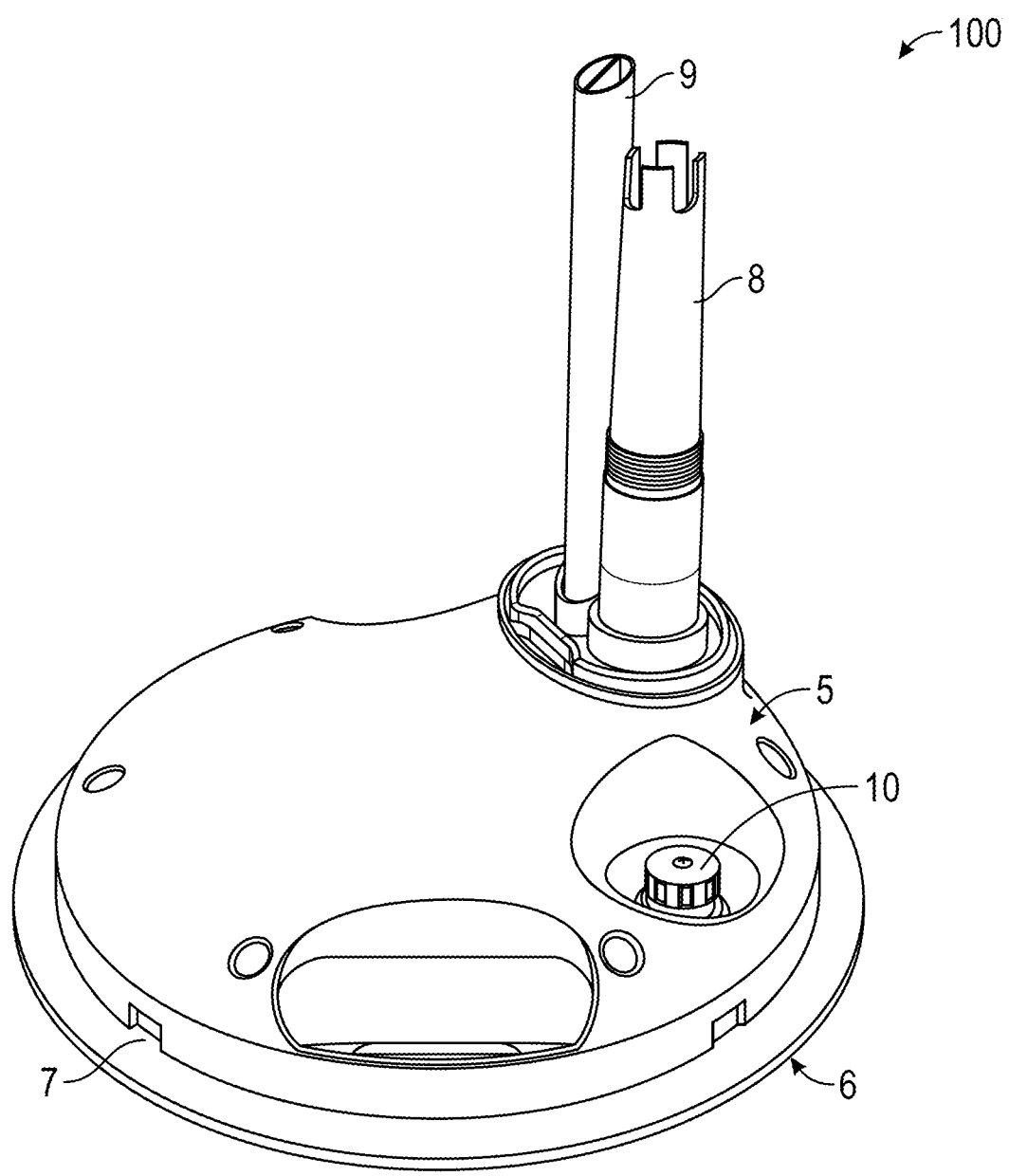
FIG. 2 is a bottom perspective view of an exemplary embodiment of the smart pool skimmer, in accordance with certain aspects of the present disclosure.

FIG. 2 is a bottom perspective view of an exemplary embodiment of the smart pool skimmer 100, in accordance with certain aspects of the present disclosure. In the exemplary embodiment, the smart pool skimmer 100 includes the integrated ORP/pH/Temperature Sensor 8, water level sensor 9 and USB charging port 10.

Figure 3:
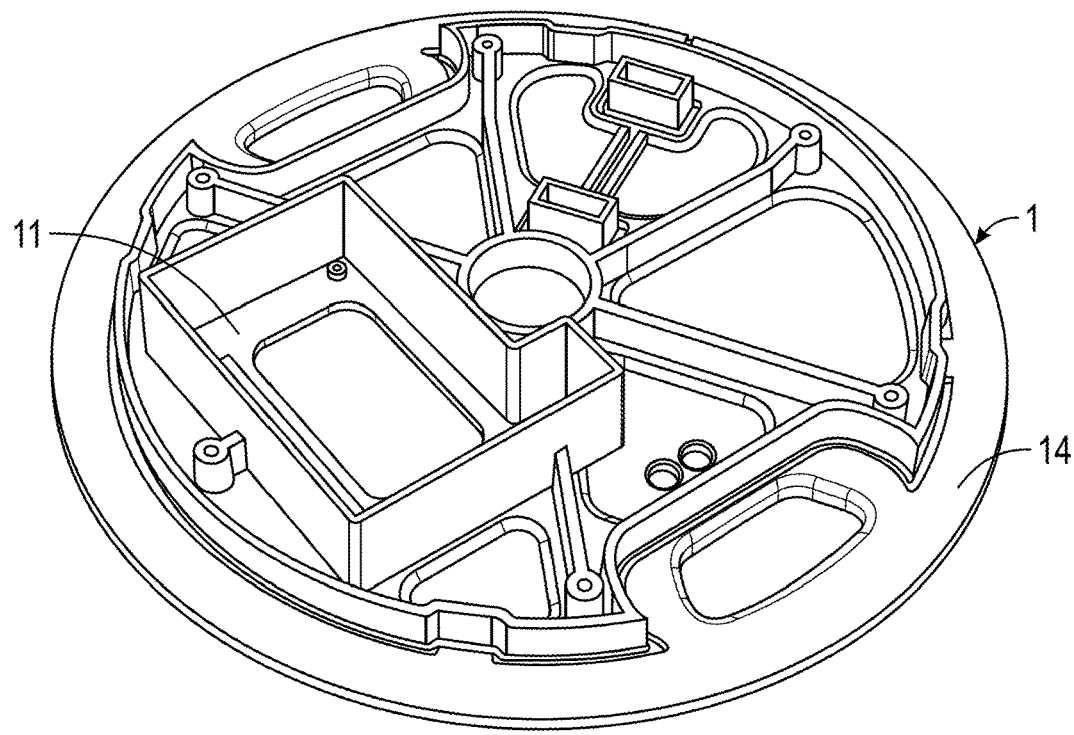
FIG. 3 is a bottom view of the top cover of an exemplary embodiment of the smart pool skimmer, in accordance with certain aspects of the present disclosure.

FIG. 3 is a bottom view of the top cover of an exemplary embodiment of the smart pool skimmer 100, in accordance with certain aspects of the present disclosure. The top cover 1 includes the electronics compartment 11 which houses two primary components: the power source (not illustrated) and primary control board (not illustrated). In one exemplary embodiment, the control board and power source are sealed with an encapsulation compound. The control board will include four LEDs 30 which will transmit light through the upward facing light pipe 4. The light pipe is bonded or insert molded into the top cover as a watertight seal.

Figure 4:
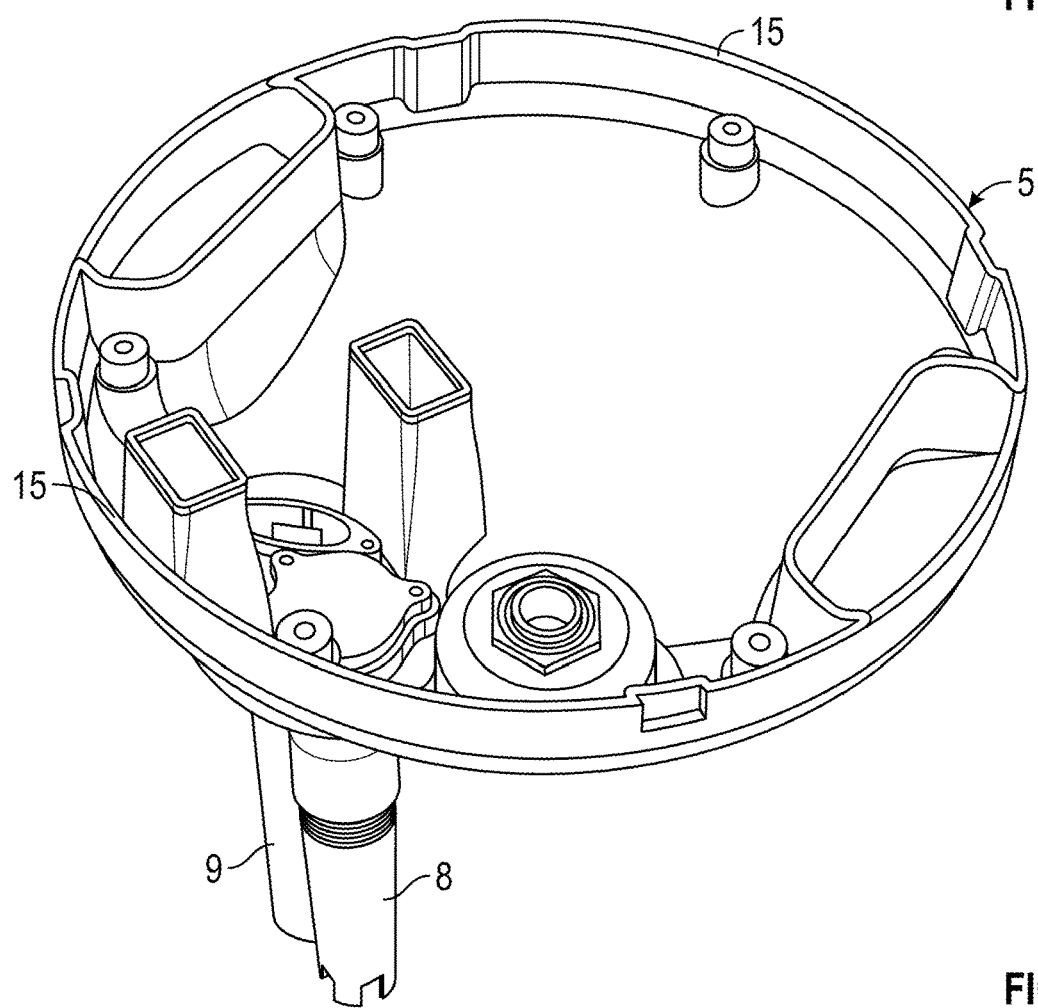
FIG. 4 is an exploded view of the bottom cover of an exemplary embodiment of the smart pool skimmer, in accordance with certain aspects of the present disclosure.

FIG. 4 is a top view of the bottom cover 5 of an exemplary embodiment of the smart pool skimmer, in accordance with certain aspects of the present disclosure.

FIG. 5 illustrates an electronics architecture schematic of an exemplary embodiment of the smart pool skimmer, in accordance with certain aspects of the present disclosure. The solar panel 20 acts as a power source to the system and is regulated through a charge controller 22. The power source can include a rechargeable battery 24 that provides power as required in non or restricted sunlight conditions. A microcontroller 26 connects to the sensors 28, which are both digital and analog depending on their function, through sensor circuitry 32. In one exemplary embodiment, the microcontroller 26 stores data locally or sends the data to the cloud when a Wi-Fi and/or cellular connection are present. In the exemplary embodiment, the microcontroller 26 runs a real-time operating system that enables it to take advantage of low-power modes, concurrent processing, and advanced pipelining, which can allow the smart pool skimmer to run advanced models on real-time data, without disrupting observation of measurements by the sensors.

In an exemplary embodiment, the smart pool skimmer's microcontroller 26 uses a communication unit 34 to communicate with other devices, such as a mobile device or any other computing device. The communication unit can use Bluetooth, Bluetooth Low Energy (BLE), Wi-Fi, cellular or any other type of communication protocol currently available or later developed to communicate with other devices. Because the microcontroller 26 is in communication with the communication unit 34 and therefore other devices, the software and firmware of the smart pool skimmer can be upgraded, can transmit near real-time measurement information of the sensors 28, and can be reconfigured and/or recalibrated when needed.

In one exemplary embodiment, the smart pool skimmer generates power through a solar panel; however in sunlight restricted areas, the skimmer uses alternative power sources, including a rechargeable or replaceable battery 24, or hydropower via a micro-turbine. In an alternative embodiment, the micro-turbine would attach to the bottom cover 5 and utilize the water flow entering the skimmer as a source of hydropower.

In another exemplary embodiment, the smart pool skimmer can be a part of the pool monitoring system. An exemplary pool monitoring system comprises the pool skimmer as disclosed herein, a cloud-based analytics server in communication with the pool skimmer using a computer network, such as the Internet, and a user computing device with a graphical user interface for visualization of trend-based conditions of the pool water. The smart pool skimmer transmits information regarding conditions of the pool water to the server using the communication unit of the smart pool skimmer, and the cloud-based analytics server tracks the conditions of the pool water. The cloud-based analytics server, using machine learning algorithms, takes in current and historical sensor data to predict behavior of the pool chemistry, water level, and chemical reactions to alert users of the exemplary pool monitoring system of upcoming events. The development of the machine learning algorithms is performed in the cloud using big data aggregation tools that train the models of the machine learning algorithms. The data gathered from the sensors of the smart pool skimmer can easily show patterns and trends because the data reflects biological cycles such as temperature rising and falling, sunlight for a predicted time of day, and evaporation constants that correlate with temperature. Based on the data patterns and trends, highly accurate machine learning models are developed, and are sent to the user computing devices to run in an "offline" mode. The user computing devices can run machine learning algorithms using live data and can make predictions, even while offline.

In another embodiment, the user computing device of the pool monitoring system has third-party software that receives and uses the information regarding pool conditions, instead of the graphical user interface.

In yet another embodiment, because the smart pool skimmer is uniquely positioned at a boundary condition of air and water, the smart pool skimmer includes an acoustic transducer to Wi-Fi or Bluetooth thereby making the smart pool skimmer a unique instrument for communicating via Wi-Fi underwater. Because of the local processing power, the smart pool skimmer can use Fast Fourier Transforms (FFTs) and other acoustic sampling techniques that make communicating and detecting sound waves underwater easily possible at low power levels. The acoustic transducer enables the smart pool skimmer to be a central hub for processing and acoustic sensing.

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, cc, 3 and c-c-c or any other ordering of a, b, and c).

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but are to be accorded the full scope consistent with the language of the claims, wherein reference to an element in the singular is not intended to mean "one and only one" unless specifically so stated, but rather "one or more." Unless specifically stated otherwise, the term "some" refers to one or more. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112(f) unless the element is expressly recited using the phrase "means for" or, in the case of a method claim, the element is recited using the phrase "step for."

It is to be understood that the claims are not limited to the precise configuration and components illustrated above. Various modifications, changes, and variations may be made in the arrangement, operation and details of the methods and apparatus described above without departing from the scope of the claims.

What is claimed is:

1. A pool skimmer unit, comprising:
    a body comprising:
        a top cover, and
        a bottom cover;
    a controller unit disposed between the top cover and the bottom cover, and
    a sensor fairing coupled to the bottom cover of the body and comprising openings therethrough so that an interior of the sensor fairing is in fluid communication with an exterior of the sensor fairing; at least one sensor disposed inside the sensor fairing, the at least one sensor connected to the controller unit through an annulus in the bottom cover of the body, the at least one sensor secured and sealed to the body through the annulus and configured to detect a water level within the interior of the sensor fairing; and
    a communication unit in communication with the controller unit.

2. The pool skimmer unit of claim 1, further comprising an indicator light.

3. The pool skimmer unit of claim 1, wherein the at least one sensor is configured to detect pH.

4. The pool skimmer unit of claim 1, wherein the at least one sensor is configured to detect oxidation reduction potential (ORP).

5. The pool skimmer unit of claim 1, wherein the at least one sensor is configured to detect temperature.

6. The pool skimmer unit of claim 1, wherein the at least one sensor comprises a solid-state water level sensor.

7. The pool skimmer unit of claim 1, wherein the at least one sensor is configured to detect water movement.

8. The pool skimmer unit of claim 1, wherein the communication unit uses Bluetooth, Wi-Fi, or combination thereof.

9. The pool skimmer unit of claim 1, further comprising a rechargeable power unit connected to a solar panel.

10. The pool skimmer unit of claim 1, wherein the at least one sensor is configured to detect chlorine levels.

11. The pool skimmer unit of claim 1, wherein the at least one sensor is configured to detect salt concentration.

12. The pool skimmer unit of claim 1, further comprising an acoustic transducer.

13. The pool skimmer unit of claim 1, wherein the communication unit communicates with a cloud-based analytics system.

14. The pool skimmer unit of claim 1, wherein the top cover comprises a recess allowing for coupling with adaptor collars.

15. The pool skimmer unit of claim 1, wherein the at least one sensor is a tilt sensor.

16. A method of monitoring pool conditions, comprising:
    receiving and storing information of a plurality of states of pool conditions from a pool skimmer unit, the information comprising measurements from the pool skimmer unit, the pool skimmer unit comprising a body and at least one sensor disposed inside a sensor fairing, the sensor fairing coupled to a bottom cover of the body and comprising openings therethrough so that an interior of the sensor fairing is in fluid communication with an exterior of the sensor fairing, the at least one sensor configured to detect a water level within the interior of the sensor fairing; and
    tracking changes between the plurality of states of pool conditions.

17. The method of claim 16, wherein the pool conditions comprise at least one of pH, oxidation reduction potential (ORP), temperature, salt concentration, chlorine levels, pool water level, and water movement.

18. A method of monitoring pool conditions, comprising: detecting one or more of the pool conditions using one or more sensors disposed inside a sensor fairing of a pool skimmer unit, the sensor fairing comprising openings therethrough so that an interior of the sensor fairing is in fluid communication with an exterior of the sensor fairing, the one or more sensors is configured to detect water level within the pool skimmer unit; transmitting the one or more of the pool conditions to a cloud-based analytics server using a computer network; and receiving predictions regarding future pool conditions from the analytics server.

19. The method of claim 18, further comprising detecting a state of a pool pump based on the water level within the pool skimmer unit or determining a state indicative of debris accumulation within the pool skimmer unit based on the water level within the pool skimmer unit.

20. The method of claim 18, further comprising detecting a change in the one or more pool conditions; and alerting a user of the change.

* * * * *